United States Patent [19]

Gardner et al.

[11] Patent Number: 4,876,048
[45] Date of Patent: Oct. 24, 1989

[54] PURIFICATION OF ALKANESULFONYL CHLORIDES

[75] Inventors: David M. Gardner, Worcester Township, Montgomery County, Pa.; Gregory A. Wheaton, Logan Township, Gloucester County, N.J.; Martin Nosowitz, Easttown Township, Chester County, Pa.

[73] Assignee: Pennwalt Corporation, Philadelphia, Pa.

[21] Appl. No.: 283,113

[22] Filed: Dec. 12, 1988

[51] Int. Cl.$^4$ ............................................. C07C 143/70
[52] U.S. Cl. ................................ 562/828 R; 833; 834
[58] Field of Search ................................... 260/543 R

[56] References Cited

U.S. PATENT DOCUMENTS

| | | | |
|---|---|---|---|
| 2,667,507 | 1/1954 | Jones et al. | 260/513 |
| 2,842,588 | 7/1958 | Honeycutt | 260/504 |
| 3,147,303 | 9/1964 | Krefeld et al. | 260/543 |
| 3,232,975 | 2/1966 | Merkel | 260/456 |
| 3,248,423 | 4/1966 | Stratton | 260/543 |
| 3,413,337 | 11/1968 | Bost | 260/513 |
| 3,479,398 | 11/1969 | Bost et al. | 260/513 |
| 3,485,870 | 12/1969 | Bost | 260/513 |
| 4,549,993 | 10/1985 | McElligott, Jr. | 260/543 R |

FOREIGN PATENT DOCUMENTS 2504235 5/1976 Fed. Rep. of Germany .

OTHER PUBLICATIONS

J. Chem. Soc., 4547–4555 (1957), "Barnard: Oxidation of Organic Sulphides".
PB–257 891, Aug. 1976, "Reaction Kinetics of Ozone with Sulfur Compounds", Montana Univ., Missoula Dept. of Chemistry.

*Primary Examiner*—Paul J. Killos

[57] ABSTRACT

An ozone-containing gas is used for removing oxidizable odorous impurities and color from alkanesulfonyl chlorides.

8 Claims, No Drawings

PURIFICATION OF ALKANESULFONYL CHLORIDES

BACKGROUND OF THE INVENTION

This invention relates to a process for removing color-forming and odorous impurities from alkanesulfonyl chlorides.

In the large scale production of alkanesulfonyl chlorides by oxidation of alkane thiols or dialkyl disulfides, it is desirable but extremely difficult to achieve complete oxidation of the odorous organosulfur impurities without overoxidation. Overoxidation with chlorine results in unwanted side-chain chlorination. On the other hand, underoxidation allows small amounts of the undesirable odorous oxidizable sulfur compounds to remain. These compounds may include the starting alkane thiols and dialkyl sulfides, as well as dialkyl sulfides, and alkyl alkanethiosulfonates. These and other impurities cause significant unpleasant odor and lead to the formation of color. Further, odor or color may develop when the alkanesulfonyl chloride or its aqueous dispersion is subsequently used as a reactant or solvent.

PRIOR ART

U.S. Pat. No. 3,232,975 discloses a process for bleaching sulfonic acid and their derivatives using a chlorinated cyanuric acid. U.S. Pat. No. 4,549,993 discloses a method of purifying crude liquid organosulfonyl chloride by scrubbing with aqueous HCl. U.S. Pat. No. 3,147,303 discloses a process for refining alkanesulfonyl chlorides using oxygen-containing acids of hexavalent sulfur or anhydrides of such acids. U.S. Pat. No. 3,248,423 discloses a method of preparing alkane sulfonyl chlorides, one step of which employs a small percentage of oxygen to inhibit undesirable chlorination of the alkyl group of the alkane sulfonyl chloride.

BRIEF SUMMARY OF THE INVENTION

This invention is a process for removing oxidizable odorous impurities and color from alkanesulfonyl chlorides by contacting said alkanesulfonyl chlorides with an ozone-containing gas within a temperature range of about 0° C. to about 100° C.

DETAILED DESCRIPTION

The alkanesulfonyl chlorides which may be treated by the process of this invention are those having the general formula $RSO_2Cl$ wherein R is an alkyl group of 1 to 20 carbon atoms. The alkanesulfonyl chloride may be substantially solvent-free or it may be in combination with aqueous or non-aqueous inert solvents.

The method of this invention is employed to remove color-forming or odorous impurities, or both. It is effective for removing various impurities from alkanesulfonyl chlorides including alkanethiols of the general formula RSH, dialkyl sulfides of the general formula $RSR^1$, dialkyl sulfides of the general formula $RSSR^1$, dialkyl disulfoxides of the general formula $RSOR^1$, alkyl alkanethiolsulfinates of the general formula $RS(O)SR^1$, and alkyl alkanethiolsulfonates of the general formula $RSO_2SR^1$, where R and $R^1$ is selected from alkyl of 1 to 20 carbon atoms and can the same or different.

This method depends on the selection of the appropriate conditions of temperature and contact time. It can be used at temperatures from about 0° C. to about 100° C. The preferred treatment temperature is from about 30° C. to 70° C. The treatment time is selected to provide the desired product purity and can be determined by continuous or frequent monitoring of color or impurity concentration. In general, the treatment time required will be sufficient to reduce odorous and color-forming impurities and preferably from 10 minutes up to 8 hours.

Ozone concentrations of about 0.001% to 10% by weight may be used. The ozone may be contained in oxygen, air or another carrier gas that is inert to the alkanesulfonyl chloride such as nitrogen or helium. The preferred ozone concentration will depend upon the concentration of impurities present in the alkanesulfonyl chloride, the temperature and the desired time for treatment. The preferred ozone concentration is from about 0.05% to 4.0% by weight. The ozone can be generated in air or oxygen by various methods known to those skilled in the art.

The process of the invention is carried out either batchwise or in a continuous fashion and can be performed with or without agitation. Mechanical agitation of the alkanesulfonyl chloride is preferred. The mechanical agitation can be by stirring or forced circulation of the alkanesulfonyl chloride. The ozone-containing gas may be vented after a single pass through the alkanesulfonyl chloride, or it may be recycled to the ozone generator. The ozone present in the gas mixture which is vented can be decomposed by passing the mixture through a column of activated carbon, or by other methods known to those skilled in the art.

The alkanesulfonyl chlorides to be treated with ozone may be substantially anhydrous, contain water or may be dispersed in water or an inert organic solvent. Suitable organic solvents which are inert to the alkanesulfonyl chloride which may be employed including low boiling alkanes such as n-hexane, n-heptane and n-octane, and chlorinated hydrocarbons such as chloroform. It is preferred that the alkanesulfonyl chlorides which are liquids at the temperature of treatment are treated as neat liquids and those which are solids can be mixed with an inert solvent and treated as a solution.

Some advantages of this process include little or no dilution and little or no addition of bulk impurities, rapid decomposition of the ozone to molecular oxygen and, unlike chlorine, no overoxidation of the alkanesulfonyl chloride to sulfate or chlorinated alkanesulfonyl chlorides.

As used herein and in the claims, the term alkyl group of 1 to 20 carbon atoms means a straight, branched chain or cyclic alkyl group which may be substituted or unsubstituted with one or more other atoms or functional groups. Such substituents include, for example, halogen, hydroxyl, carboxylic acid and ether.

The following examples further illustrate the process of this invention.

EXAMPLES

The treatment apparatus used to carry out the process of the Examples consisted of a glass vessel filled with 50 ml. of the sample to be treated immersed in a thermostated temperature bath. A fritted glass sparging tube was inserted into the vessel and gas sparged through the liquid sample at a rate of 230 ml./min. No other mixing was provided. Color was determined by optical measurements made by a spectrophotometer at 450 m. and correlated to the APHA color scale (ASTM D-1209-

84). The APHA color scale is based on the concentration of a platinum-cobalt complex in aqueous solution which imparts a yellow color to the solution. The APHA scale has a range of values from 0 to 500, with 0 corresponding to pure water (no discernible color) and 500 to a dark yellow solution containing 500 ppm of the platinum-cobalt complex. Since the spectrophotometer is capable of making accurate measurements above the highest APHA color number, an extrapolation was performed.

EXAMPLE 1

To a 50 ml. sample of methanesulfonyl chloride was added methyl methanethiosulfonate to an arbitrary concentration of 1270 ppm. The sample was ozonized in the apparatus described above for 256 minutes at 60° C. with air containing 0.1% w/w ozone. After ozonation, analysis by gas chromatograph with a flame photometric detector (configured to be sensitive only to sulfur-containing compounds) revealed that only 29 ppm methyl methanethiosulfonate was left.

EXAMPLE 2

To a sample of methanesulfonyl chloride was added methyl methanethiosulfonate and dimethyl disulfide to a final concentration of about 1000 ppm of each and split into several 50 ml. samples. One sample was ozonized in the apparatus described above for 120 minutes at 60° C. with air containing 0.1% w/w ozone. After ozonation, analysis by gas chromatography with a flame photomeric detector for sulfur-containing compounds showed 120 ppm methyl methanethiolsulfonate and less than 1 ppm dimethyl disulfide remained. A second 50 ml. sample was ozonized in the apparatus described above at 22° C. for 120 minutes and was found to contain 460 ppm methyl methanethiosulfonate and 3 ppm dimethyl disulfide. A third 50 ml. sample was ozonized for 60 minutes at 22° C. and was found to contain 910 ppm methyl methanethiosulfonate and 4 ppm dimethyl disulfide. A fourth 50 ml. sample was ozonized for 60 minutes at 60° C. and was found to contain 530 ppm methyl methanethiosulfonate and 4 ppm dimethyl disulfide. A fifth 50 ml. sample was treated with air only at the same flow rate, 230 ml./min., as the four ozonized samples, at 60° C. for 90 minutes, and was found to contain 670 ppm methyl methanethiosulfonate and 170 ppm dimethyl disulfide. It may be deduced from these results that the dimethyl disulfide contained in these solutions is rapidly oxidized by the treatment, that some of the dimethyl disulfide is oxidized to methyl methanethiosulfonate, and that longer times and higher temperatures of treatment allow more complete removal of oxidizable sulfur-containing impurities.

EXAMPLE 3

A 50 ml. sample of dark yellow methanesulfonyl chloride (APHA 790) was placed into the apparatus described above and ozonized at 60° C. for 60 minutes with 0.1% ozone in air. The treated methanesulfonyl chloride was nearly water-white (APHA 500).

The present invention may be embodied in other specific forms without departing from the spirit of the invention, and the foregoing examples are not intended to limit the scope of the invention.

I claim:

1. A process for removing odorous and color-forming impurities from alkanesulfonyl chlorides comprising contacting said alkanesulfonyl chlorides with an ozone-containing gas at a temperature ranging from about 0° C. to about 100° C. for a time sufficient to reduce odorous and color-forming impurities therein.

2. The process of claim 1 wherein said ozone-containing gas has an ozone concentration ranging from about 0.001% to about 10% by weight.

3. The process of claim 2 wherein said alkanesulfonyl chloride is contacted with said ozone-containing gas for about 10 minutes to about 8 hours.

4. The process of claim 1 wherein said alkanesulfonyl chloride has the general formula $RSO_2Cl$ where R represents an alkyl group of 1 to 20 carbons contained in a straight or branched chain.

5. The process of claim 4 wherein R is substituted by halogen, hydroxyl, lower alkyl ether, alkylcarbonyloxy, nitro or phosphoro.

6. The process of claim 4 wherein R is methyl.

7. The process of claim 3 wherein the temperature of treatment is from about 30° C. to about 70° C. and the ozone-containing gas has an ozone concentration ranging from about 0.05% to about 4% by weight.

8. The process of claim 7 wherein the contact time ranges from about 10 minutes to about 4 hours.

* * * * *